United States Patent [19]

Cognacq

[11] 4,156,009
[45] May 22, 1979

[54] DIAZEPINE DERIVATIVES

[75] Inventor: Jean-Claude Cognacq, Garches, France

[73] Assignee: Hexachimie, Rueil Malmaison, France

[21] Appl. No.: 890,410

[22] Filed: Mar. 27, 1978

[30] Foreign Application Priority Data

Mar. 31, 1977 [GB] United Kingdom ............... 13587/77

[51] Int. Cl.$^2$ ..................... A61K 31/38; C07D 513/04; A61K 31/55
[52] U.S. Cl. ............................. 424/275; 260/239.3 B; 260/465 R; 260/332.3 R; 260/332.2 R
[58] Field of Search ................. 260/239.3 B; 424/273

[56] References Cited

U.S. PATENT DOCUMENTS

| 3,669,959 | 6/1972 | Hromatka et al. ............ 260/239.3 B |
| 3,806,512 | 4/1974 | Nakanishi et al. ............ 260/239.3 B |
| 3,849,405 | 11/1974 | Nakanishi et al. ............ 260/239.3 B |
| 3,859,275 | 1/1975 | Nakanishi et al. ............ 260/239.3 B |
| 3,872,089 | 3/1975 | Hromatka et al. ............ 260/239.3 B |

*Primary Examiner*—John M. Ford
*Assistant Examiner*—Robert T. Bond
*Attorney, Agent, or Firm*—Poms, Smith, Lande & Glenny

[57] ABSTRACT

The invention relates to 6-cyclopropyl-1,3-dihydro-1-methyl-5-phenyl-2-oxo-2H-thieno [2,3-e] diazepine and pharmaceutically acceptable non-toxic acid addition salts, these compounds being useful as medicaments particularly for the treatment of gastro-duodenyl disorders. A synthesis for the diazepine is also described.

9 Claims, No Drawings

DIAZEPINE DERIVATIVES

The present invention relates to 6-cyclopropyl-1,3-dihydro-1-methyl-5-phenyl-2-oxo-2H-thieno[2,3-e]diazepine of formula I, and its pharmaceutically acceptable non-toxic acid addition salts.

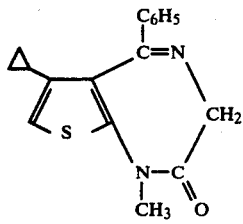

The present invention also provides a method of preparing 6-cyclopropyl-1,3-dihydro-1-methyl-5-phenyl-2-oxo-2H-thieno [2,3-e]diazepine (I), comprising (a) reacting cyclopropylmethylketone with benzoylacetonitrile in the presence of acetic acid to form 2-benzoyl-3-cyclopropylcrotonitrile (II), (b) cyclising the cis isomer of 2-benzoyl-3-cyclopropylcrotonitrile with sulphur to obtain 2-amino-3-benzoyl-4-cyclopropylthiophene (III), (c) reacting the 2-amino-3-benzoyl-4-cyclopropylthiophene with bromoacetyl bromide to form 3-benzoyl-2-(α-bromoacetamido)-4-cyclopropylthiophene (IV), (d) reacting the 3-benzoyl-2-(α-bromoacetamido)-4-cyclopropylthiophene with ammonia to obtain 2-(α-aminoacetamido)-3-benzoyl-4-cyclopropylthiophene (V), (e) cyclosing the obtained 2-(α-aminoacetamido)-3-benzoyl-4-cyclopropylthiophene to obtain 6-cyclopropyl-1,3-dihydro-5-phenyl-2-oxo-2H-thieno[2,3-e]diazepine (VI), (f) metallating 6-cyclopropyl-1,3-dihydro-5-phenyl-2-oxo-2H-thieno[2,3-e]diazepine to form a 1-metallo derivative thereof, and (g) reacting the metallo derivative with a methylating agent to produce the desired compound which may optionally be transformed into an acid addition salt.

The 1-metallo derivative is preferably the 1-sodium derivative which may be produced by reaction of the 6-cyclopropyl-1,3-dihydro-5-phenyl-2-oxo-2H-thieno[2,3-e]diazepine with sodium hydride, sodium methoxide or sodium ethoxide, the reaction preferably being conducted at ambient temperature in a mixture of benzene and dimethylformamide.

The methylating agent which is reacted with the 1-metallo derivative is preferably methyl iodide or methyl sulphate. It is preferred to carry out the methylation reaction at ambient temperature with stirring.

The reaction of stage (a) for the preparation of compound II leads to a cis and transmixture thereof and it is the cis isomer (i.e. the isomer in which the methyl group and nitrile group are cis to each other) which is required for the succeeding steps of the method. The isomers may be separated by chromatographing on alumina using diethyl ether as the eluent.

The reaction of stage (a) is preferably conducted in benzene. Preferably also the cyclisation of stage (b) is conducted in ethanol, preferably in the presence of triethylamine.

Ether is the preferred solvent for stage (c) and the reaction is preferably conducted in the presence of pyridine.

Tetrahydrofuran is the preferred solvent for the amination reaction of stage (d) and the cyclisation reaction of stage (e) is preferably effected by heating under reflux in toluene in the presence of acetic acid.

An overall reaction sequence for the preparation of the compound (I) starting from cyclopropylmethylketone and benzoylacetonitrile is shown in the following reaction scheme.

REACTION DIAGRAM

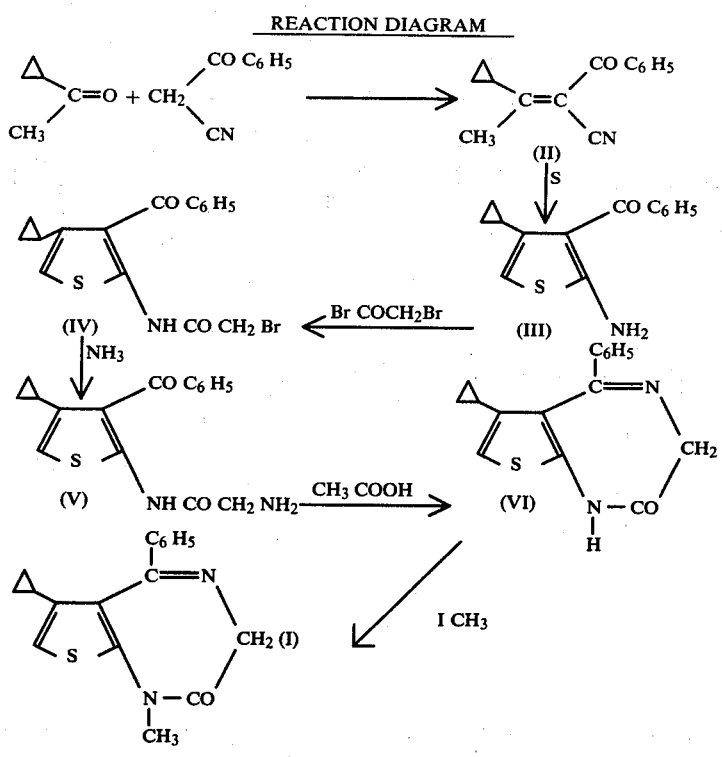

Compound I according to the invention has pharmacological properties which make it therapeutically useful and in particular it has a protective action on the gastro-intestinal tract.

The present invention also relates to this therapeutic use of compound I and its non-toxic acid salts which can be administered pharmacologically.

The preparation of the product of the invention is described in the following examples.

EXAMPLE 1

2-Benzoyl-3-cyclopropylcrotonitrile (Formula II)

A mixture of 1.52 moles cyclopropylmethylketone, 1.22 moles benzoylacetonotrile, 122 cm³ acetic acid, 12 g β-alanine, and 600 cm³ anhydrous benzene is heated under reflux for 12 hours, whilst eliminating the water as it is formed with a Dean-Stark apparatus. The mixture obtained is left to cool, washed with water, dried over magnesium sulphate and the benzene is evaporated under vacuum. The residue is taken up in a minimum of ether, the solution is passed over a column of 1200 g basic alumina, the column is eluted with ether (5 liters) and the solvent is evaporated from the eluate under vacuum. 150 g of a clear yellow oil are obtained, which are used without further purification for the subsequent reactions.

EXAMPLE 2

2-Amino-3-benzoyl-4-cyclopropylthiophene (Formula III)

A mixture of:

150 g 2-benzoyl-3-cyclopropylcrotonitrile prepared in Example 1,
23 g sulphur,
160 cm³ triethylamine,
300 cm³ pure ethyl alcohol is stirred for 8 hours.

200 cm³ water are then added to the mixture dropwise, with stirring, the mixture is then stirred for 1 hour. The mixture is then centrifuged, washed with a 50/50 mixture of alcohol/water and dried.

107 g of the expected product are obtained, having a melting point of 132° C.

EXAMPLE 3

3-Benzoyl-2-(α-bromoacetamido)-4-cyclopropylthiophene (Formula IV)

39 cm³ bromoacetyl bromide are added dropwise, with stirring, to a solution of 90 g 2-amino-3-benzoyl-4-cyclopropylthiophene prepared in Example 2 and 32 cm³ pyridine in 1000 cm³ ether, in order to maintain a slight reflux. The mixture is stirred for 4 hours at ambient temperature, then poured onto ice, decanted, washed with water, the organic phase is dried over magnesium sulphate and the ether is evaporated under vacuum. The evaporation residue is taken up in 300 cm³ petroleum ether and 60 cm³ ether. A trituration process follows, the solid obtained is centrifuged, washed with petroleum ether and dried to obtain 100 g of the expected product having a melting point of 82°–84° C.

EXAMPLE 4

2-(α-Aminoacetamido)-3-benzoyl-4-cyclopropylthiophene (Formula V)

90 g 3-benzoyl-2-(α-bromoacetamido)-4-cyclopropylthiophene prepared in Example 3 are dissolved in 400 cm³ tetrahydrofuran and ammonia is bubbled into the solution thus obtained for 2 hours, then the latter is left for 24 hours. The tetrahydrofuran is evaporated under vacuum, the residue taken up in 250 cm³ chloroform, washed with water, the chloroform solution is dried with magnesium sulphate and the chloroform is evaporated under vacuum, to give 74 g of the expected product in the form of an oil which is used without further purification for the subsequent reactions.

EXAMPLE 5

6-Cyclopropyl-1,3-dihydro-5-phenyl-2-oxo-2H-thieno[2,3-e]diazepine (Formula VI)

The mixture of:

71 g 2-(α-aminoacetamido)-3-benzoyl-4-cyclopropylthiophene, prepared in Example 4,
1000 cm³ toluene
2 cm³ acetic acid is heated under reflux for 3 hours.

The toluene is evaporated under vacuum, the residue taken up in 200 cm³ chloroform, washed with dilute ammonia, then with water, dried over magnesium sulphate and the chloroform evaporated under vacuum. The residue is dissolved in 200 cm³ acetone, hydrochloric ether is added to the solution with stirring to give a pH of 1 and left for 2 hours. The solution is filtered, washed with acetone and dried to give 55 g of the hydrochloride of the expected product having a melting point of 264° C.

To obtain the base, 55 g hydrochloride are placed in suspension with stirring in 200 cm³ water, the latter is made alkaline by the slow addition of ammonia and then stirred for 1 hours, then centrifuged, washed with water and dried to obtain 44 g of the expected product having a melting point of 160° C.

EXAMPLE 6

6-Cyclopropyl-1,3-dihydro-1-methyl-5-phenyl-2-oxo-2H-thieno[2,3-e]diazepine (Formula I)

9 g 50% sodium hydride in vegetable oil are added with stirring in small portions to a solution of 42 g 6-cyclopropyl-1,3-dihydro-5-phenyl-2-oxo-2H-thieno[2,3-e]diazepine prepared in Example 5 dissolve in a mixture of 200 cm³ anhydrous dimethylformamide and 200 cm³ anhydrous benzene, the latter is then stirred for 4 hours at ambient temperature.

30 g methyl iodide are added slowly drop by drop to the solution, with vigorous stirring. When the thermal effect has ceased, the latter is stirred for 5 hours at ambient temperature. The mixture obtained is poured onto ice, extracted with ether, washed with water, dried over magnesium sulphate and the ether is evaporated under vacuum. The evaporation residue is taken up in 250 cm³ acetone. Hydrochloric ether is added with stirring to give a pH of 1, the mixture is then stirred for 1 hour, filtered, washed with acetone and dried to give 37.5 g hydrochloride of the expected product with a melting point of 238° C.

The pharmacological properties of the hydrochloride of 6-cyclopropyl-1,3-dihydro-1-methyl-5-phenyl-2-oxo-2H-thieno[2,3-e]diazepine are shown in the following tests:

I—PROTECTIVE ACTIVITY AS REGARDS ULCERS CAUSED BY PHENYLBUTAZONE

Method

Male rats, of the OFA strain, weighing 160-180 g are placed on a diet of water 24 hours before the oral administration of the product studied (1 cm³/100 g). 30 minutes later, the rats receive 150 mg/kg phenylbutazone (1 cm³/100 g) orally.

The stomachs are removed 6 hours after the last treatment. Each stomach is classified according to the following scale:
  0: no ulcers
  1: 1 to 2 ulcers
  2: 3 to 4 ulcers
  3: more than 4 ulcers.

The average of the results for a batch, multiplied by the percentage of rats having ulcers in this batch, gives an ulceration index whose maximum is 300.

The following Table I gives the ulceration indices and the protective dose 50 ($PD_{50}$) which corresponds to the index 150.

TABLE I

| Product of Example 6 mg/kg orally | Ulceration Index |
| --- | --- |
| 16 | 240 |
| 32 | 179 |
| 64 | 62 |
| 128 | 29 |
| $PD_{50}$ mg/kg orally | 39 |

II—ACTIVITY ON SHAY ULCERS

Method

Male rats of the OFA strain, weighing 190-210 g, receive a solution of 20% glucose and 9% sodium chloride as their only food for 3 days.

Under an ether anaesthetic, the pylorus is tied, while taking care not to include blood vessels in the binding. The tested product is administered intraperitoneally and the stomach is removed 2 hours after the binding. The gastric liquid is collected and the following parameters are measured:
  volume
  pH
  free acidity (potentiometry)
  total acidity (potentiometry)
  peptic activity (hydrolysis of albumen of oxen and measurement of the tyrosine liberated).

The number of ulcers in the rumen are counted.

The following Table II gives the value of the parameters measured.

TABLE II

| Product of Example 6 mg/kg intraperitoneally | pH | Secretion Volume in cm³ | Acidity free in mEq/l | free ds the secretion | total in mEq/l | total ds the secretion | Pepsin in mg/cm³ | in mg ds secretion | Ulcers |
| --- | --- | --- | --- | --- | --- | --- | --- | --- | --- |
| 0 | 1.14 | 5.6 | 97 | 534 | 114 | 630 | 0.68 | 3.70 | 0 |

TABLE II-continued

| Product of Example 6 mg/kg intraperitoneally | pH | Secretion Volume in cm³ | Acidity free in mEq/l | Acidity free ds the secretion | Acidity total in mEq/l | Acidity total ds the secretion | Pepsin in mg/cm³ | Pepsin in mg ds secretion | Ulcers |
|---|---|---|---|---|---|---|---|---|---|
| | ±0.02 | ±0.6 | ±4 | ±53 | ±4 | ±61 | ±0.04 | ±0.35 | |
| 8 | 1.19 | 4.0 | 91 | 388 | 109 | 459 | 0.67 | 2.66 | 0 |
| | ±0.05 | ±0.3 | ±9 | ±53 | ±8 | ±56 | ±0.04 | ±0.26 | |
| | ns | * | ns | ns | ns | ns | ns | * | |
| 16 | 1.21 | 2.7 | 82 | 275 | 102 | 335 | 0.67 | 1.83 | 0 |
| | ±0.05 | ±0.52 | ±9 | ±54 | ±9 | ±65 | ±0.05 | ±0.39 | |
| | ns | ** | ns | ** | ns | ** | ns | ** | |
| 32 | 1.67 | 1.7 | 56.5 | 145 | 80 | 189 | 0.64 | 1.14 | 0 |
| | ±0.23 | ±0.33 | ±13.3 | ±55 | ±11 | ±57 | ±0.04 | ±0.18 | |
| | * | *** | ** | *** | ** | *** | ns | *** | |

*p < 0.05
**p < 0.01
***p < 0.001

III—ACUTE TOXICITY

The lethal dose $LD_{50}$, determined orally in the rat, of the compound of Example 6, is 915 mg/kg.

Since the protective dose $PD_{50}$ is 39 mg/kg (c.f. Table I), the ratio of toxicity/activity or therapeutic index is approximately 23, which represents a very interesting therapeutic margin.

In conclusion, the compound of Example 6 has properties which protect the gastro-intestinal tract. It may be used to treat humans for gastro-duodenal disorders (ulcers), in an appropriate form of dosage for oral administration in particular in the form of capsules containing a dose of 100 mg, the daily dose varying from 100 to 300 mg.

What I claim is:

1. A pharmaceutical composition useful for the treatment of gastro-duodenal disorders containing, as the active ingredient, a gastro-duodenal protective effective amount of 6-cyclopropyl-1,3-dihydro-1-methyl-5-phenyl-2-oxo-2H-thieno[2-3-e] diazepine or a pharmaceutically acceptable non-toxic acid addition salt thereof in combination with a pharmaceutically acceptable non-toxic excipient.

2. A pharmaceutical composition according to claim 1 wherein the active ingredient is present in an effective amount for oral administration.

3. A pharmaceutical composition according to claim 2 wherein said composition is in capsule form.

4. A pharmaceutical composition according to claim 3 wherein the capsule contains 100 mg of active ingredient.

5. A method of treating gastro-duodenal disorders comprising administering to a patient a gastro-duodenal pretective effective amount of a medicament selected from the group consisting of 6-cyclopropyl-1,3-dihydro-1-methyl-5-phenyl-2-oxo-2H-thieno[2,3-e]diazepine and pharmaceutically acceptable non-toxic addition salts thereof.

6. A method as claimed in claim 5 wherein the medicament is administered orally.

7. A method as claimed in claim 6 wherein the medicament is in the form of a capsule.

8. A method as claimed in claim 7 wherein the capsule contains a dose of 100 mg of the medicament.

9. A method as claimed in claim 5 wherein the medicament is administered in a daily dose of 100 to 300 mg.

* * * * *